United States Patent
Gray et al.

(10) Patent No.: US 9,433,639 B2
(45) Date of Patent: *Sep. 6, 2016

(54) SYNTHETIC MECHANICAL HEMOSTATIC COMPOSITION, METHOD OF MAKING AND USE THEREOF

(71) Applicant: Poly-Med, Inc., Anderson, SC (US)

(72) Inventors: Kenneth David Gray, Clemson, SC (US); Michael Scott Taylor, Anderson, SC (US)

(73) Assignee: Poly-Med, Inc., Anderson, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/511,608

(22) Filed: Oct. 10, 2014

(65) Prior Publication Data
US 2015/0023905 A1 Jan. 22, 2015

Related U.S. Application Data

(63) Continuation of application No. 13/445,855, filed on Apr. 12, 2012, now Pat. No. 8,858,980.

(51) Int. Cl.
| | | |
|---|---|---|
| *A61F 2/00* | (2006.01) |
| *A61K 31/765* | (2006.01) |
| *A61K 38/14* | (2006.01) |
| *A61K 38/39* | (2006.01) |
| *A61K 31/407* | (2006.01) |
| *A61K 31/65* | (2006.01) |
| *A61K 31/7036* | (2006.01) |
| *A61K 31/7056* | (2006.01) |
| *A61K 33/42* | (2006.01) |
| *A61K 31/7048* | (2006.01) |
| *A61L 24/00* | (2006.01) |
| *A61L 24/04* | (2006.01) |
| *C08G 63/64* | (2006.01) |
| *A61K 31/166* | (2006.01) |
| *A61K 45/06* | (2006.01) |
| *C08G 64/18* | (2006.01) |

(52) U.S. Cl.
CPC ........... *A61K 31/765* (2013.01); *A61K 31/166* (2013.01); *A61K 31/407* (2013.01); *A61K 31/65* (2013.01); *A61K 31/7036* (2013.01); *A61K 31/7048* (2013.01); *A61K 31/7056* (2013.01); *A61K 33/42* (2013.01); *A61K 38/14* (2013.01); *A61K 38/39* (2013.01); *A61K 45/06* (2013.01); *A61L 24/0015* (2013.01); *A61L 24/0042* (2013.01); *A61L 24/046* (2013.01); *C08G 63/64* (2013.01); *C08G 64/18* (2013.01); *A61L 2300/404* (2013.01); *A61L 2400/04* (2013.01)

(58) Field of Classification Search
None
See application file for complete search history.

(56) References Cited

U.S. PATENT DOCUMENTS 6,385,491 B1 * 5/2002 Lindemans .......... A61N 1/0587
424/423
2006/0142736 A1 * 6/2006 Hissink ................ A61F 11/002
604/540

* cited by examiner

*Primary Examiner* — Susan Tran

(57) ABSTRACT

A biocompatible, polymeric composition is disclosed. The composition comprises a base polymer comprising (i) a prepolymer comprising para-dioxanone (PDO) and trimethylene carbonate (TMC); and (ii) an end-graft polymer chain comprising a polylactone. Also disclosed are a method for treating bleeding from bone or bony structures using the composition, a method for filling a void or correct a defect in a bone using the composition, and a method for producing the biocompatible, polymeric composition of the present application.

25 Claims, 1 Drawing Sheet

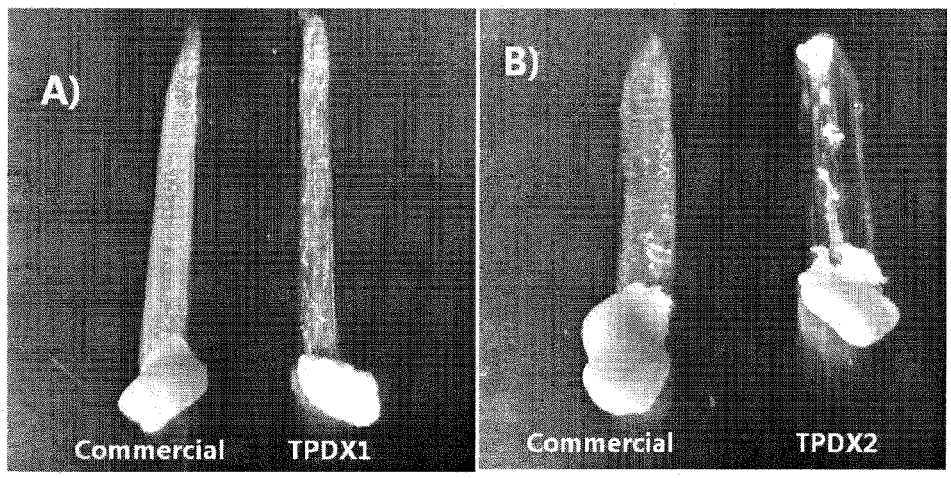

SYNTHETIC MECHANICAL HEMOSTATIC COMPOSITION, METHOD OF MAKING AND USE THEREOF

The present application is a continuation of U.S. application Ser. No. 13/445,855, filed Apr. 12, 2012, which issued as U.S. Pat. No. 8,858,980 on Oct. 14, 2014, all of which are hereby incorporated herein in their entirety by reference.

FIELD

The present application relates generally to a synthetic composition, and more specifically, to synthetic mechanical hemostatic compositions that are suitable for a variety of medical applications.

BACKGROUND

Surgical bone wax is a relatively safe and inert hemostatic agent that is commonly used in a variety of surgical procedures to mechanically plug bleeding bony structures and elicit immediate hemostasis. Since commercial bone wax typically consists of beeswax, isopropyl palmitate and softening agents such as paraffin, the material is minimally resorbable and remains in the body for the lifetime of the patient following surgery.

The continued post-operative persistence of bone wax is the most critical issue regarding the potential for future complications. There have been case reports of bone wax-related complications that include the development of post-thoractomy paraplegia and tumor. The persistent foreign bone wax may also result in immune responses to the bone wax. Furthermore, the residual bone wax can migrate out of the original site of application following surgery. Migrated bone wax can exert compressive forces on the spinal cord, leading to debilitating paraplegia that requires a second operative procedure to remove the displaced bone wax. Accordingly, there exits a need for the development a bone wax that is biocompatible and has similar physical properties to conventional bone wax.

SUMMARY

One aspect of the present application relates to a biocompatible, polymeric composition. The biocompatible, polymeric composition comprises a base polymer comprising (i) a prepolymer or first polymeric segment comprising paradioxanone (PDO) and trimethylene carbonate (TMC); and (ii) an end-graft polymer chain or second polymeric segment comprising a polylactone. In further embodiments, the end-graft polymer chain or second polymeric segment comprises semicrystalline polylactone chain segments. In yet other embodiments, the polymeric compositions are sterile, and optionally, do not contain beeswax or other animal or human products (such as, for example, collagen).

Another aspect of the present application relates to a method for treating bleeding from bone or bony structures. The method comprises the step of administering to a site of bleeding from bone or bony structures in a subject an effective amount of the biocompatible, polymeric composition of the present application.

Another aspect of the present application relates to a method for filling a void or correct a defect in a bone. The method comprises administering to a void or defect in a bone of a subject an effective amount of the biocompatible, polymeric composition of the present application, such that the void is filled or the defect is corrected.

Another aspect of the present application relates to a method for producing the biocompatible, polymeric composition of the present application. The method comprises the steps of: forming a prepolymer by admixing para-dioxanone and trimethylene carbonate and polymerizing with an initiator; and end-capping the prepolymer with a composition comprising a polylactone.

BRIEF DESCRIPTION OF DRAWINGS

FIG. 1 is a composite showing streak test comparison of commercial ETHICON® bone wax vs. (A) TPDX1 and (B) TPDX2.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. In addition, the disclosures of all patents and patent applications referenced herein are incorporated by reference in their entirety.

In case of conflict, the present specification, including definitions, will control. Following long-standing patent law convention, the terms "a," "an" and "the" mean "one or more" when used in this application, including in the claims.

One aspect of the present application relates to a synthetic biocompatible composition that comprises a base polymer comprising a prepolymer and an end-graft polymer In some embodiments, the end-graft polymer comprises a polylactone.

In some embodiments, the synthetic biocompatible composition further comprises a biocompatible plasticizer. In some embodiments, the synthetic biocompatible composition further comprises one or more therapeutic agents. In some embodiments, the synthetic biocompatible composition is a mechanical hemostatic polymeric composition that is entirely synthetic and does not contain any animal products, such as bees wax. In other embodiments, the synthetic biocompatible composition is sterile.

In certain embodiments, the synthetic biocompatible composition can be used as a substitute for traditional bone wax. The synthetic biocompatible composition is biocompatible and preferably bioabsorbable. When used as a bone wax in a surgical procedure, it does not increase the infection rate normally associated with the procedure, does not interfere with bone healing and does not cause additional inflammation beyond those normally associated with the procedure.

The Base Polymers

The base polymer is a biocompatible polymer comprising a prepolymer and end-grafted polymeric chain segments. The term "biocompatible" as used herein is intended to describe materials that do not elicit a substantial detrimental response in vivo. In some embodiments, the biocompatible polymer is also a "bioabsorbable polymer." The teen "bioabsorbable polymer" refers to a polymer that can be broken down by either chemical or physical process in an in vivo setting, upon interaction with the physiological environment at a treatment site, and erodes or dissolves within a period of time. The rate of degradation is mostly determined by the chemical structure of the polymer, as well as the local environment. A bioabsorbable polymer serves a temporary function in the body, such as plugging bleeding bony structures and eliciting immediate hemostasis, or delivering a drug, and is then degraded or broken into components that are metabolizable or excretable.

Examples of bioabsorbable polymers include, but are not limited to, polyglycolic acid (PGA), polylactic acid (PLA), lactic acid-glycolic acid copolymer (PLGA), polyethylene terephthalate (PET), polyglycolide-lactide, polycaprolactone (PCL), lactic acid-ε-caprolactone copolymer (PLCL), polydioxanone (PDO), polytrimethylene carbonate (PTMC), polydioxanone, polyoxalate and copolymers thereof.

Suitable bioabsorbable polyester copolymers include, but are not limited to, lactide/glycolide copolymers, caprolactone/glycolide copolymers, lactide/trimethylene carbonate copolymers, lactide/glycolide/caprolactone terpolymers, lactide/glycolide/trimethylene carbonate terpolymers, lactide/caprolactone/trimethylene carbonate terpolymers, glycolide/caprolactone/trimethylene carbonate terpolymers, and lactide/glycolide/caprolactone/trimethylene carbonate terpolymers.

In other embodiments, the bioabsorbable polymer comprises polyaxial, segmented co-polymers with non-crystallizable, flexible components of the chain at the core and rigid, crystallizable segments at the chain terminals. The bioabsorbable polymers are produced by reacting amorphous polymeric polyaxial initiators with cyclic monomers. The amorphous polymeric polyaxial initiators have branches originating from a polyfunctional organic compound so as to extend along more than two coordinates and to copolymerize with the cyclic monomers. In some embodiments, the bioabsorbable copolymer comprises at least 30%, 50%, 65%, 75%, 90% or 95% by weight, of a crystallizable component which is made primarily of glycolide-derived or L-lactide-derived sequences.

In some embodiments, the amorphous polymeric, polyaxial initiators are made by reacting a cyclic monomer or a mixture of cyclic monomers such as trimethylene carbonate (TMC), caprolactone, and 1,5-dioxapane-2-one in the presence of an organometallic catalyst with one or more polyhydroxy, polyamino, or hydroxyamino compound having three or more reactive amines and/or hydroxyl groups. Typical examples of the latter compounds are glycerol and ethane-trimethylol, propane-trimethylol, pentaerythritol, triethanolamine, and N-2-aminoethyl-1,3-propanediamine.

The flexible polyaxial prepolymer can be derived from para-dioxanone, 1,5-dioxepan-2-one, or one of the following mixtures of polymers: (1) trimethylene carbonate and para-dioxanone with or without a small amount of glycolide; (2) trimethylene carbonate and a cyclic dimer of para-dioxanone with or without a small amount of glycolide; (3) caprolactone and para-dioxanone with or without a small amount of glycolide; (4) trimethylene carbonate and caprolactone with or without a small amount of D,L-lactide; (5) caprolactone and D,L-lactide (or meso-lactide) with or without a small amount of glycolide; and (6) trimethylene carbonate and D,L-lactide (or meso-lactide) with or without a small amount of glycolide. Further, the crystallizable segment can be derived from para-dioxanone. Alternate precursors of the crystallizable segment can be a mixture of predominantly para-dioxanone with a minor component of one or more of the following monomers: glycolide, L-lactide 1,5-dioxepan-2-one, trimethylene carbonate, and caprolactone.

In other embodiments, the bioabsorbable polymer is an ABA-type triblock polymer, where A is L-lactide/glycolide and B is PEG. In certain embodiments, the absorbable polymer fiber comprises a polyaxial, segmented biodegradable copolyester. In other embodiments, the absorbable polymer comprises a L-lactide/caprolactone copolymer, a L-lactide/trimethylene carbonate copolymer, a glycolide/L-lactide/trimethylene carbonate copolymer copolymer, a L-lactide/caprolactone/trimethylene carbonate copolymer or combinations thereof. In one embodiment, the absorbable polymer comprises a homopolymer of polydioxanone. In another embodiment, the absorbable polymer comprises a glycolide/L-lactide/trimethylene carbonate copolymer. In another embodiment, the absorbable polymer comprises a PEG/glycolide/L-lactide copolymer.

In some other embodiments, the bioabsorbable polymer is a uniaxial polymer. Examples of uniaxial polymers include, but are not limited to, a homopolymer of polydioxanone, poly glycolic acid, polyglycolide, polylactide (L-, D-, or meso-), trimethylene carbonate, polycaprolactone, and copolymers thereof.

In certain embodiments, the bioabsorbable polymer is a solid crystalline polyaxial coplyomer comprising a polyaxial prepolymer and semicrystalline end graft, which is referred to herein after as TPDX polymer. The term "semicrystalline" refers to a crystallinity of greater than 5 J/g as measured by differential scanning calorimetry (DSC). In some embodiments, the term "semicrystalline" refers to a crystallinity of 20-70 J/g as measured by differential scanning calorimetry (DSC).

In some embodiments, the polyaxial prepolymer comprises polymerized trimethylene carbonate (TMC) and para-dioxanone (PDO) and is initiated with trimethylopropane; while the end graft comprises polymerized L-lactide and para-dioxanone. The prepolymer constitutes approximately 10-40%, preferably 15-35%, more preferably 20-30%, most preferably 25% by mole of the bioabsorbable polymer. The end-graft constitutes approximately 60-90%, preferably 65-85%, more preferably 70-80%, most preferably 75% by mole of the bioabsorbable polymer. In one embodiment, the composition of the prepolymer is TMC/PDO (17.1/8.6% by mole), and the end graft composition is L-lactide/PDO (5.9/68.3% by mole).

In other embodiments, the polyaxial prepolymer comprises polymerized trimethylene carbonate (TMC) and para-dioxanone (PDO) and is initiated with trimethyopropane; while the end graft comprises polymerized glycolide and para-dioxanone. The prepolymer constitutes approximately 10-40%, preferably 15-35%, more preferably 20-30%, most preferably 25-26% by mole of the bioabsorbable polymer. The end-graft constitutes approximately 60-90%, preferably 65-85%, more preferably 70-80%, most preferably 74-75% by mole of the bioabsorbable polymer. In one embodiment, the composition of the prepolymer is TMC/PDO (16.7/8.3% by mole), and the end graft composition is glycolide/PDO (11.2/63.8% by mole). In another embodiment, the prepolymer constitutes approximately 25% by mole of the bioabsorbable polymer, the end-graft constitutes approximately 75% by mole of the bioabsorbable polymer, and the composition of the prepolymer is TMC/PDO (17.1/8.6% by mole), and the end graft composition is glycolide/PDO (4.5/69.8% by mole).

In other embodiments, the prepolymer consists of polymerized PDO, glycolide and trimethylene carbonate (TMC) and is initiated with trimethylolpropane. The end graft consists of polymerized glycolide and para-dioxanone. The prepolymer constitutes approximately 30-60%, preferably 35-55%, more preferably 40-50%, most preferably 45% by mole of the polymer, and the end-graft constitutes approximately 40-70%, preferably 45-65%, more preferably 50-60%, most preferably 55% by mole. In one embodiment, the composition of the prepolymer is glycolide/TMC/PDO (14.8/14.5/15.8% by mole), and the end graft composition is glycolide/PDO (8.2/46.8% by mole).

The amount of initiator (e.g., trimethylopropane) may vary in different crystalline polyaxial copolymer preparations. The larger is the amount of the initiator, the smaller is the molecular weight of the copolymer. In some embodiments, the prepolymer is prepared with a monomer-to-initiator mole ratio in the range of 30:1 to 100:1. In one embodiment, the prepolymer is prepared with a monomer-to-initiator mole ratio in the range of 35:1. In another embodiment, the prepolymer is prepared with a monomer-to-initiator mole ratio in the range of 100:1.

In other embodiments, the prepolymer consists of polymerized PDO and trimethylene carbonate (TMC), and the end-graft polymer comprises a polylactone. In one embodiment, the end-graft polymer further comprises para-dioxanone. In another embodiment, the polylactone comprises a poly L-lactide. In another embodiment, the polylactone comprises a poly-glycolide. In other embodiments, the polylactone is a polymer other than poly L-lactide or polyglycolide. For example, in one embodiment, the polylactone comprises a copolymer of (1) para-dioxanone repeat units and (2) repeat units of at least one other cyclic monomer. In a related embodiment, the at least one other cyclic monomer is selected from the group consisting of L-lactide, D-lactide, D,L-lactide, glycolide, caprolactone and trimethylene carbonate.

In other embodiments, the TPDX polymer is a solid crystalline polyaxial copolymer comprising a polyaxial prepolymer, semicrystalline end graft and a third outer segment comprising poly(trimethylene carbonate). In one embodiment, such a bioabsorbable polymer is prepared by reacting (1) a purified polyaxial copolymer comprising a polyaxial prepolymer of para-dioxanone and trimethylene carbonate initiated with trimethylolpropane, and semicrystalline end graft consists of polymerized glycolide and para-dioxanone with (2) trimethylene carbonate. In some embodiments, the purified polyaxial copolymer is reacted with trimethylene carbonate at a weight ratio of 1:1 to 9:1. In one embodiment, the purified polyaxial copolymer is reacted with trimethylene carbonate at a weight ratio of 3:1.

In some embodiments, the absorbable polymer comprises two or more different types of TPDX polymers. For instance, a highly crystalline TPDX may be blended with a less crystalline and semi-liquid TPDX to yield a compliant putty-like blend. In other embodiments, the absorbable polymer comprises a TPDX polymer with other absorbable polyesters, such as polyaxial poly(TMC) and/or low molecular weight poly(para-dioxanone).

In some embodiments, the number average molecular weight (Mn) of the base polymer is in the range of 3000-10,000 dalton, preferably in the range of 4000-7000 dalton. In other embodiments, the weight average molecular weight (Mw) of the base polymer is in the range of 5000-20,000 dalton, preferably in the range of 8000-13000 dalton. The base polymer needs to be semicrystalline in order to have handling integrity. The higher is the crystallinity of the polymer, the more plasticizer is needed to soften the polymer so that the biocompatible, polymeric composition would have physical properties similar to conventional bone wax.

The Plasticizers

Plasticizers are additives that increase the plasticity or fluidity of a material. Suitable plasticizers for the present application include, but are not limited to, polyalkylene glycols (PAG) such as polyethylene glycol (PEG) and polypropylene glycol (PPG). Suitable molecular weight of PEG for plasticizing the bioabsorbable polymer of the present application (e.g., TPDX polymers) include PEG with a number average molecular weight in the range of 1,000-20,000 dalton, preferably in the range of 2,000-15,000 dalton. In one embodiment, the PEG has a number average molecular weight of 15,000 dalton. In other embodiments, the PEG has a number average molecular weight of 1,000 or 4,600 dalton. In other embodiments, the PEG has a weight average molecular weight of 1,000-4,000 dalton. In some embodiments, the polymer-to-plasticizer weight ratio in the biocompatible, polymeric composition is in the range of 1000:1 to 1:1, preferably in the range of 100:1 to 3:1. In some embodiments, biocompatible, polymeric composition formulations with desired compliant handling characteristics (i.e., feel like a putty) are prepared by combining a purified solid form of the base polymer (e.g., TPDX) which is usually in powder form following purification, with 1-25% w/w of PEG.

The Therapeutic Agents

The therapeutic agents may include anti-inflammatory agents, anti-adhesion agents, osteogenesis and calcification promoting agents, antibacterial agents and antibiotics, immunosuppressive agents, immunostimulatory agents, anesthetics, cell/tissue growth promoting factors, anti-scarring agents, anti-neoplastic and anticancer agents.

Examples of anti-inflammatory agents include, but are not limited to, non-steroidal anti-inflammatory drugs such as ketorolac, naproxen, diclofenac sodium and flurbiprofen.

Examples of anti-adhesion agents include, but are not limited to talcum powder, metallic beryllium and oxides thereof, copper, silk, silica, crystalline silicates, talc, quartz dust, and ethanol.

Examples of osteogenesis or calcification promoting agents include, but are not limited to, bone fillers such as hydroxyapatite, tricalcium phosphate, and calcium sulfate, bone morphogenic proteins (BMPs), such as BMP-2, BMP-3, BMP-4, BMP-5, BMP-6, and BMP-7.

Examples of antibacterial agents and antibiotics include, but are not limited to, erythromycin, penicillins, cephalosporins, doxycycline, gentamicin, vancomycin, tobramycin, clindamycin and mitomycin.

Examples of immunosuppressive agents include, but are not limited to, glucocorticoids, alkylating agents, antimetabolites, and drugs acting on immunophilins such as ciclosporin and tacrolimus.

Examples of immunostimulatory agents include, but are not limited to, interleukins, interferon, cytokines, toll-like receptor (TLR) agonists, cytokine receptor agonist, CD40 agonist, Fc receptor agonist, CpG-containing immunostimulatory nucleic acid, complement receptor agonist, or an adjuvant.

Examples of antiseptics include, but are not limited to, chlorhexidine and tibezonium iodide.

Examples of anesthetic include, but are not limited to, lidocaine, mepivacaine, pyrrocaine, bupivacaine, prilocaine, and etidocaine.

Examples of cell growth promoting factors include, but are not limited to, epidermal growth factors, human platelet derived TGF-β, endothelial cell growth factors, thymocyte-activating factors, platelet derived growth factors, fibroblast growth factor, fibronectin or laminin.

Examples of antineoplastic/anti-cancer agents include, but are not limited to, paclitaxel, carboplatin, miconazole, leflunamide, and ciprofloxacin.

Examples of anti-scarring agents include, but are not limited to cell-cycle inhibitors such as a taxane, immunomodulatory agents such as serolimus or biolimus (see, e.g., paras. 64 to 363, as well as all of US 2005/0149158, which is incorporated by reference in its entirety).

It is recognized that in certain forms of therapy, combinations of agents/drugs in the same polymeric composition can be useful in order to obtain an optimal effect. Thus, for example, an antibacterial and an anti-inflammatory agent may be combined in a single copolymer to provide combined effectiveness.

Method of making the Biocompatible Polymeric Composition

The base polymers suitable for the biocompatible polymeric composition of the present application can be synthesized as described in the Examples of the present application. In some embodiments, the biocompatible polymeric composition of the present application is produced by blending one or more bioabsorbable polymers with the proper amount of a plasticizer. In other embodiments, the biocompatible polymeric composition of the present application is produced by forming a prepolymer by admixing para-dioxanone and trimethylene carbonate and polymerizing with an initiator; and end-capping the prepolymer with a composition comprising a polylactone. Biocompatible polymeric compositions containing a therapeutic agent can be prepared by the cold-worked or hot-worked method as described in Example 13 of the present application, depending on the heat-resistance of the therapeutic agent. For therapeutic agents that are likely to be inactivated by heat, the cold-worked method is preferred. Briefly, the biocompatible polymeric composition is completely melted in the absence of the therapeutic agent. The melted composition is cooled to room temperature or below to delay crystallization of the polymer in the composition. In certain embodiments, the cooling is conducted at a rate of about 10° C. per minute. The therapeutic agent is then added to the melted composition at room temperature or below and mixed thoroughly with the composition to create a homogeneous blend.

Methods of Using the Biocompatible Polymeric Composition

Another aspect of the present application relates to a method for treating bleeding from bone or bony structures. The method comprises the step of administering to a site of bleeding from bone or bony structures in a subject an effective amount of the biocompatible, polymeric composition of the present application.

Another aspect of the present application relates to a method for filling a void or correct a defect in a bone. The method comprises administering to a void or defect in a bone of a subject an effective amount of the biocompatible, polymeric composition of the present application, such that the void is filled or the defect is corrected.

Another aspect of the present application relates to a method of delivering therapeutic agents using the biocompatible, polymeric composition of the present application. The method comprises the step of applying an effective amount of the biocompatible, polymeric composition comprising a base polymer and one or more therapeutic agents at a treatment site. The method can be used to effectively plug bleeding bony structures and eliciting immediate hemostasis, and for the treatment of conditions such as sternal wound infection (SWI) and osteomylitis.

Another aspect of the present application relates to a method of reducing the likelihood of sternal wound infection (SWI). The method comprises the step of administering to a sternal wound site an effective amount of the biocompatible, polymeric composition comprising a base polymer and one or more anti-infection agents.

SWI is a common complication following cardiothoracic surgery and poses a high risk of morbidity and mortality. Mediastinitis is reported to occur in up to 5% of patients following cardiac surgery (Baskett R. J. et al. *Ann Thorac Surg*, 67, 462 (1999)), and approximately 15% of patients are readmitted for a recurrent sternal wound infection (Kaye, A. E. et al. *Ann Plast Surg*, 64, 658 (2010)). Infections are often the result of staphylococcal bacteria, and unfortunately, treatment of SWI involves an invasive procedure of surgical debridement (Douville, E. C. et al. *Ann Thorac Surg*, 78, 1659 (2004)). A number of risk factors have been identified for SWI (Baskett R. J. et al., supra); however, the only modifiable factors include the use of bone wax and the use of bilateral mammary arteries in diabetic patients. The use of bone wax in thoracic surgery can be employed as an aid in prophylactic treatment in addition to the conventional role of bone wax as a hemostatic agent to plug the bleeding sternum. By incorporating antibiotics such as rifampin, which has been shown to improve outcomes against staphylococcal SWI (Khanlari, B. et al. *J Antimicrob Chemother*, 65, 1799 (2010)), bone wax can be engineered as a prophylactic material for use in cardiothoracic surgery.

The present invention is further illustrated by the following examples which should not be construed as limiting. The contents of all references, patents and published patent applications cited throughout this application, as well as the Figures and Tables are incorporated herein by reference.

EXAMPLES

Example 1

Composition of TPDX Copolymers

TPDX1: A solid, crystalline polyaxial copolymer comprising a polyaxial prepolymer and semicrystalline end graft. The prepolymer consists of polymerized para-dioxanone and trimethylene carbonate and is initiated with trimethylolpropane. The end graft consists of polymerized L-lactide and para-dioxanone. The prepolymer constitutes approximately 25% by mole of the polymer, and the end-graft constitutes approximately 75% by mole. The composition of the prepolymer is TMC/PDO (17.1/8.6% by mole), and the end graft composition is L-lactide/PDO (5.9/68.3% by mole).

TPDX2: A solid, crystalline polyaxial copolymer comprising a polyaxial prepolymer and semicrystalline end graft. The prepolymer consists of polymerized para-dioxanone and trimethylene carbonate and is initiated with trimethylolpropane. The end graft consists of polymerized glycolide and para-dioxanone. The prepolymer constitutes approximately 25% by mole of the polymer, and the end-graft constitutes approximately 75% by mole. The composition of the prepolymer is TMC/PDO (17.1/8.6% by mole), and the end graft composition is glycolide/PDO (4.5/69.8% by mole).

TPDX3: A solid, crystalline polyaxial copolymer comprising a polyaxial prepolymer and semicrystalline end graft. The prepolymer consists of polymerized para-dioxanone and trimethylene carbonate and is initiated with trimethylolpropane. The end graft consists of polymerized glycolide and para-dioxanone. The prepolymer constitutes approximately 25% by mole of the polymer, and the end-graft constitutes approximately 75% by mole. The composition of the prepolymer is TMC/PDO (17.1/8.6% by mole), and the end graft composition is glycolide/PDO (4.5/69.8% by mole). The monomer to initiator ratio is increased in TPDX3 to increase its molecular weight relative to TPDX1.

TPDX5: A solid, crystalline polyaxial copolymer comprising a polyaxial prepolymer and semicrystalline end graft, and a third outer segment consisting of poly(trimethylene carbonate). This composition is prepared by taking purified TPDX3 and reacting with trimethylene carbonate to extend the polymer chains with amorphous segments. This polymer has been prepared by reacting 60.0 grams of TPDX3 with 20.0 grams of trimethylene carbonate.

TPDX6: A solid, crystalline polyaxial copolymer comprising a polyaxial prepolymer and semicrystalline end graft. The prepolymer consists of polymerized para-dioxanone, glycolide and trimethylene carbonate and is initiated with trimethylolpropane. The end graft consists of polymerized glycolide and para-dioxanone. The prepolymer constitutes approximately 45% by mole of the polymer, and the end-graft constitutes approximately 55% by mole. The composition of the prepolymer is Glycolide/TMC/PDO (14.8/14.5/15.8% by mole), and the end graft composition is glycolide/PDO (8.2/46.8% by mole).

TPDX7: A solid, crystalline polyaxial copolymer comprising a polyaxial prepolymer and semicrystalline end graft. The prepolymer consists of polymerized para-dioxanone and trimethylene carbonate and is initiated with trimethylolpropane. The end graft consists of polymerized glycolide and para-dioxanone. The prepolymer constitutes approximately 25-26% by mole of the polymer, and the end-graft constitutes approximately 74-75% by mole. The composition of the prepolymer is TMC/PDO (16.7/8.3% by mole), and the end graft composition is glycolide/PDO (11.2/63.8% by mole.).

Example 2

Synthesis of TPDX1

A reaction setup comprising a three-neck round bottom flask, a stainless steel stirrer, a Teflon stirring adapter, and two gas inlet adapters was assembled and tested by reducing the pressure of the assembly with a vacuum pump to less than 0.5 mm Hg. When acceptable vacuum was obtained, the assembly was purged with nitrogen gas and trimethylene carbonate (37.0 grams), p-dioxanone (18.5 grams, thawed) and trimethylolpropane (8.1 grams) were added to the reaction assembly through a glass funnel. The reaction materials were then dried at 40° C. and 0.15 mm Hg for one hour. The assembly was purged with nitrogen gas, and the temperature was raised to 100° C. to melt reaction materials. Stirring was initiated upon melting to mix the reaction materials, and then Tin (II) Ethyl hexanoate (1.05 mL, 0.2M in toluene) was added to the flask. The temperature was increased to 140° C. to initiate polymerization. As the reaction proceeded at 140° C., samples were taken for analysis by gel permeation chromatography (GPC) to determine the extent of conversion. The reaction was stopped after 3.5 hours and cooled to room temperature overnight. The next day, the temperature was increased from room temperature to 100° C., and the second charge consisting of p-dioxanone (147.4 grams) and L-lactide (18.1 grams) was added through a glass funnel to the reaction flask. The reaction contents were stirred for 45 minutes at 100° C. to mix thoroughly, and then the temperature was increased to 140° C. in order to initiate the synthesis of the end-graft onto the prepolymer. After 4.5 hours, the temperature was decreased to room temperature. The final product was collected and <analyzed by GPC and differential scanning calorimetry (DSC).

Example 3

Synthesis of TPDX2

A reaction setup comprising a three-neck round bottom flask, a stainless steel stirrer, a Teflon stirring adapter, and two gas inlet adapters was assembled and tested by reducing the pressure of the assembly with a vacuum pump to less than 0.5 mm Hg. When acceptable vacuum was obtained, the assembly was purged with nitrogen gas and trimethylene carbonate (34.1 grams), p-dioxanone (17.0 grams, thawed) and trimethylolpropane (7.466 grams) were added to the reaction assembly through a glass funnel. The reaction materials were then dried at room temperature and 0.05 mm Hg for 30 minutes. The assembly was purged with nitrogen gas, and the temperature was raised to 115° C. to melt reaction materials. Stirring was initiated upon melting to mix the reaction materials, and then Tin (II) Ethyl hexanoate (0.944 mL, 0.2M in toluene) was added to the flask. The temperature was increased to 140° C. to initiate polymerization. As the reaction proceeded at 140° C., samples were taken for analysis by gel permeation chromatography (GPC) to determine the extent of conversion. The reaction was allowed to continue overnight at 140° C. The next day, a second charge consisting of p-dioxanone (138.9 grams) and glycolide (10.1 grams) was added through a glass funnel to the reaction flask. The reaction proceeded at 140° C. for 6 hours, and then the temperature was decreased to 100° C. and held at that temperature for 17 hours. While still hot, the polymer was poured out of the reaction flask into a clean jar. The final product was analyzed by GPC and differential scanning calorimetry (DSC).

Example 4

General Method for Purification of TPDX-Type Copolymers

The unpurified polymer was dissolved in dichloromethane using a concentration of 0.25 grams polymer per 1 mL of solvent. 100 mL of this solution was blended with approximately 400 mL of cold isopropyl alcohol (−60° C. to −70° C.), causing polymer to precipitate. The precipitated polymer was filtered, and then the polymer was blended again with cold isopropyl alcohol (−60° C. to −70° C.), using approximately 250 mL of solvent. The purified polymer was dried in a fume hood for a minimum of 12 hours, and then the polymer was transferred to a vacuum oven to dry further in order to remove any remaining isopropyl alcohol.

Example 5

General Method for Purification of TPDX-Type Copolymers

The unpurified polymer was dissolved in acetone using a concentration of 0.25 grams polymer per 1 mL of solvent. 100 mL of this solution was blended with approximately 400 mL of cold isopropyl alcohol (−60° C. to −70° C.), causing polymer to precipitate. The precipitated polymer was filtered, and then the polymer was blended again with cold isopropyl alcohol (−60° C. to −70° C.), using approximately 250 mL of solvent. The purified polymer was dried in a fume hood for a minimum of 12 hours, and then the polymer was transferred to a vacuum oven to dry further in order to remove any remaining isopropyl alcohol.

Example 6

Alternate General Method for Purification of TPDX-Type Copolymers

The unpurified polymer was dissolved in dichloromethane using a concentration of 0.25 grams polymer per 1.0 mL of solvent. 100 mL of this solution was blended with approximately 400 mL of cold isopropyl alcohol (−60° C. to −70° C.), causing polymer to precipitate. The precipitated polymer was filtered and added to a beaker containing approximately 200 mL of room temperature isopropyl alcohol. The mixture was stirred for approximately 60 seconds using a spatula, during which time the polymer changed from a hard solid to a semi-liquid material at the higher temperature. The isopropyl alcohol was subsequently decanted from the beaker, and the semi-liquid polymer was transferred to a sheet of foil to dry in a fume hood for a minimum of 12 hours. The purified polymer was transferred to a vacuum oven to dry further in order to remove any remaining isopropyl alcohol.

Example 7

General Method for Preparing Blend of Polymer and Therapeutic Agent(s)

Approximately 10.0 grams of polymer was heated in a clean glass jar above the melting point for at least 5 minutes until the polymer was completely molten. The jar was then moved to a freezer (−15° C.) in order to facilitate the rapid cooling of the polymer from elevated temperatures. Upon successful cooling of the polymer, the therapeutic agent(s) were added to the jar containing cold polymer and mixed thoroughly to disperse the therapeutic agent(s) throughout the polymeric matrix. The new blend was then transferred to a vacuum oven for short term storage.

Example 8

Another General Method for Preparing Blend of Polymer and Therapeutic Agent(s)

Approximately 10.0 grams of polymer was heated in a clean glass jar above the melting point for at least 5 minutes until the polymer was completely molten. The jar was then submerged in cold bath containing ice water in order to facilitate the cooling of the polymer from elevated temperatures. Upon successful cooling of the polymer, the therapeutic agent(s) were added to the cold polymer and mixed thoroughly to disperse the therapeutic agent(s) throughout the polymeric matrix. The new blend was then transferred to a vacuum oven for short term storage. (Therapeutic agents may include anti-inflammatory agents, anesthetic agents, cell growth promoting agents, antimicrobial agents (such as doxycycline, gentamicin, vancomycin, tobramycin, clindamycin, and mitomycin), antiviral agents and antineoplastic agents.)

Example 9

Method for Preparing Blend of TPDX1 with Polyethylene Glycol (AvgM$_n$=4,600)

Approximately 9.0 grams of TPDX1 was added to a clean glass jar and heated at 130° C. for 30 minutes in order to fully melt the polymer sample. Approximately 1.0 grams of Polyethylene glycol (average M$_n$=4,600) was added to the molten TPDX1 while hot and mixed thoroughly with a spatula for approximately 60 seconds. The jar was sealed with a lid, and then the blend was allowed to cool slowly to room temperature for 24 hours as it hardened.

Example 10

Method for Preparing Blend of TPDX1 with TPDX7

Approximately 5.0 grams of TPDX1 and 5.0 grams of TPDX7 were added to a clean glass jar and heated at 130° C. for 30 minutes in order to fully melt both polymers. While hot, the polymers were mixed thoroughly with a spatula for approximately 60 seconds. The jar was sealed with a lid, and then the blend was allowed to cool slowly to room temperature for 24 hours as it hardened.

Example 11

Synthesis of TPDX7: A Polyaxial, Semicrystalline, Diblock Copolymer Composed of Para-Dioxanone, Trimethylene Carbonate, and Glycolide A reaction setup comprising a three-neck round bottom flask, a stainless steel stirrer, a Teflon stirring adapter, and two gas inlet adapters was assembled and tested by reducing the pressure of the assembly with a vacuum pump to less than 0.5 mm Hg. When acceptable vacuum was obtained, the assembly was purged with nitrogen gas and trimethylene carbonate (32.8 grams), p-dioxanone (16.4 grams, thawed) and trimethylolpropane (7.393 grams) were added to the reaction assembly through a glass funnel. The reaction materials were then dried at room temperature and 0.05 mm Hg for 30 minutes. The assembly was purged with nitrogen gas, and the temperature was raised to 100° C. to melt the reaction materials. Stirring was initiated upon melting to mix the reaction materials, and then Tin (II) Ethyl hexanoate (1.0 mL, 0.2M in toluene) was added to the flask. The temperature was increased to 160° C. to initiate polymerization. As the reaction proceeded at 160° C., samples were taken for analysis by gel permeation chromatography (GPC) to determine the extent of conversion. The reaction temperature was decreased to 140° C. and was allowed to continue overnight. The next day, a second charge consisting of p-dioxanone (125.6 grams) and glycolide (25.2 grams) was added through a glass funnel to the reaction flask. The reaction proceeded at 140° C. for 8 hours, and then the temperature was decreased to 120° C. and held at that temperature for 48 hours. While still hot, the polymer was poured out of the reaction flask into a clean jar. The final product was analyzed by GPC and differential scanning calorimetry (DSC).

Example 12

DSC Analysis, GPC Analysis and Streak Test of TPDX1 and TPDX2

Purified TPDX1 and TPDX2 polymers were analyzed by differential scanning calorimetry (DSC) and gel permeation chromatography (GPC) analysis. Functional streak tests were performed on all polymers in order to qualitatively compare novel compositions to commercial ETHICON® bone wax. Streak tests were performed by kneading polymer by hand for 5 minutes to increase temperature, then spreading a streak of polymer across a clean glass surface. The spreadability of each polymer was assessed visually.

As shown in Table 1, TPDX1 melts at 70° C. with a heat of fusion equal to 53 J/g, and TPDX2 melts at 60° C. with a heat of fusion of 44 J/g. GPC analysis indicates that of the two polymers, TPDX2 had a lower polydispersity (see Table 2). Streak tests that were performed with both polymer prototypes demonstrate that TPDX1 performs more comparably to commercial bone wax. TPDX1 made a relatively clean, smooth streak across the glass plate, whereas TPDX2 produced uneven streak marks (see FIG. 1).

TABLE 1

Thermal data analysis of bone wax polymers.

| Bone Wax Formulation | Tm (° C.) | ΔH (J/g) |
|---|---|---|
| Ethicon ® Bone Wax | 54, 60 | 142 |
| TPDX1 | 70 | 53 |
| TPDX2 | 60 | 44 |

TABLE 2

GPC results for bone wax formulations.

| Composition | Mn | Mw | PDI |
|---|---|---|---|
| TPDX1 | 4,900 | 9,000 | 1.8 |
| TPDX2 | 5,500 | 7,100 | 1.3 |

Example 13

Localized Delivery of Therapeutic Agents with Synthetic Bone Wax

Formulation Preparation. Bone wax formulations were prepared by cold-worked and hot-worked methods. Cold-worked (CW) formulations were prepared by adding 1.0 gram of polymer to a glass vial that was sealed and heated at 100° C. for 30 minutes to completely melt the sample. Hot vials were quench-cooled to delay crystallization of the polymer. Vials were equilibrated at room temperature for 30 minutes, then 50 mg of test drug 1 and 50 mg of test drug 2 were added to each vial and mixed thoroughly to create a homogeneous blend. Hot-worked (HW) formulations were prepared by weighing polymer and drug and adding to the same vial at room temperature. Vials were heated at 100° C. for 30 minutes, then removed and mixed to create homogeneous formulations. Upon mixing, all polymer-drug formulations were stored immediately in a room temperature vacuum oven (vacuum >28 in. H20) for at least 24 hours.

HPLC Analysis. Test drug 1 and drug 2 were extracted from bone wax formulations using acetonitrile and analyzed by HPLC to determine drug stability. A standard solution of drug 1 and drug 2 was analyzed by HPLC and used to create a photodiode array (PDA) spectra match library. Drug stability was determined by comparison of drug 1 and drug 2 PDA spectra from the match library to the PDA spectra at appropriate retention times from exploratory extract samples. When analyzing PDA results, a match angle value below the match threshold value indicated that the exploratory PDA was statistically analogous to the match library PDA for the particular drug in question, resulting in positive molecular identification.

The results of HPLC PDA analysis are summarized in Tables 3 and 4. According to HPLC PDA analysis, extracts from cold-worked formulations contained stable drug 1 and drug 2 at T=0 and T=7 days, whereas extracts from hot-worked formulations at T=0 contained stable drug 2 and degraded drug 1. Of the two methods investigated for the preparation of bone wax-drug formulations, only cold-working resulted in a completely stable bone wax-drug formulation over 7 days. This novel material shows great promise, not only as a bioresorbable substitute for commercially available bone wax, but also as a vehicle to release prophylactic agents for the prevention of SWI.

TABLE 3

PDA results from HPLC analysis of drug 1 control sample and drug 1 extracts from hot-worked (HW) and cold-worked (CW) samples.

| Sample | Retention Time (min) | Match Angle | Match Threshold |
|---|---|---|---|
| Drug 1 Control | 15.280 | 0.095 | 1.206 |
| Drug 1, HW, T = 0 | 15.201 | 7.175 | 1.202 |
| Drug 1, CW, T = 7 | 15.306 | 0.154 | 1.201 |

TABLE 4

PDA results from HPLC analysis of drug 2 control sample and drug 2 extracts from hot-worked (HW) and cold-worked (CW) samples

| Sample | Retention Time (min) | Match Angle | Match Threshold |
|---|---|---|---|
| drug 2 Control | 6.856 | 0.027 | 1.138 |
| HW, T = 0 | 6.790 | 0.295 | 1.206 |
| CW, T = 7 | 6.855 | 0.201 | 1.136 |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A biocompatible, polymeric composition, comprising:
an absorbable polyaxial block copolymer;
wherein the absorbable polyaxial block copolymer comprises repeat units derived from cyclic monomers selected from the group consisting of para-dioxanone, L-lactide, D-lactide, D,L-lactide, glycolide, caprolactone and trimethylene carbonate;
wherein the absorbable polyaxial block copolymer further comprises an amorphous prepolymer and a semicrystalline end-graft polymer; and
wherein the amorphous prepolymer is polyaxial.

2. The biocompatible, polymeric composition of claim 1, wherein the prepolymer comprises repeat units derived from a first set of cyclic monomers selected from the group consisting of para-dioxanone, L-lactide, D-lactide, D,L-lactide, glycolide, caprolactone and trimethylene carbonate, and wherein the end-graft polymer comprises repeat units derived from a second set of cyclic monomers selected from the group consisting of para-dioxanone, L-lactide, D-lactide, D,L-lactide, glycolide, caprolactone and trimethylene carbonate.

3. The biocompatible, polymeric composition of claim 2, wherein the repeat units of the first set and the repeat units of the second set comprise the same cyclic monomers.

4. The biocompatible, polymeric composition of claims 2 and 3, wherein the repeat units of the first set include at least one additional cyclic monomer as compared to the repeat units of the second set.

5. The biocompatible, polymeric composition of claims 2 and 3, wherein the repeat units of the first set include one additional cyclic monomer as compared to the repeat units of the second set.

6. The biocompatible, polymeric composition of claim 2, wherein the repeat units of the first set include one additional cyclic monomer as compared to the repeat units of the second set, wherein both the repeat units of the first set and the second set both include glycolide.

7. The biocompatible, polymeric composition of claim 2, wherein the repeat units of the first set are not the same as the repeat units of the second set.

8. The biocompatible, polymeric composition of claim 1, wherein the prepolymer comprises repeat units derived from para-dioxanone and at least one additional monomer selected from the group consisting of L-lactide, D-lactide, D,L-lactide, glycolide, caprolactone and trimethylene carbonate.

9. The biocompatible, polymeric composition of claim 8, wherein the prepolymer comprises repeat units derived from para-dioxanone, trimethylene carbonate and at least one additional monomer selected from the group consisting of L-lactide, D-lactide, D,L-lactide, glycolide, and caprolactone.

10. The biocompatible, polymeric composition of claim 1, wherein the end-graft polymer comprises repeat units derived from para-dioxanone and at least one additional monomer selected from the group consisting of L-lactide, D-lactide, D,L-lactide, glycolide, caprolactone and trimethylene carbonate.

11. The biocompatible, polymeric composition of claim 1, wherein both the prepolymer and the end-graft polymer comprise repeat units derived from para-dioxanone and at least one additional monomer selected from the group consisting of L-lactide, D-lactide, D,L-lactide, glycolide, caprolactone and trimethylene carbonate.

12. The biocompatible, polymeric composition of claim 1, wherein both the prepolymer and the end-graft polymer comprise repeat units derived from trimethylene carbonate and at least one additional monomer selected from the group consisting of L-lactide, D-lactide, D,L-lactide, glycolide, caprolactone and para-dioxanone.

13. The biocompatible, polymeric composition of claim 1, wherein the prepolymer comprises repeat units derived from trimethylene carbonate and at least one additional monomer selected from the group consisting of para-dioxanone, glycolide, L-lactide, D-lactide, D,L-lactide, and caprolactone, and wherein the end-graft polymer comprises semi-crystalline polylactone chain segments.

14. The biocompatible, polymeric composition of claim 1, wherein the prepolymer comprises repeat units derived from trimethylene carbonate and at least one additional monomer selected from the group consisting of para-dioxanone, glycolide, L-lactide, D-lactide, D,L-lactide, and caprolactone, and wherein the end-graft polymer consists of repeat units derived from the group consisting of glycolide or L-lactide.

15. The biocompatible, polymeric composition of claim 1, wherein the prepolymer has a monomer-to-initiator mole ratio of 30:1 to 100:1.

16. The biocompatible, polymeric composition of claim 1, wherein the prepolymer comprises 10-40% by mole of the absorbable polyaxial block copolymer.

17. The biocompatible, polymeric composition of claim 1, wherein the prepolymer comprises 30-60% by mole of the absorbable polyaxial block copolymer.

18. The biocompatible, polymeric composition of claim 1, wherein the prepolymer is a copolymer comprising two types of repeat units selected from the group consisting of para-dioxanone, L-lactide, D-lactide, D,L-lactide, glycolide, caprolactone and trimethylene carbonate, and wherein the end-graft polymer is a homopolymer.

19. The biocompatible, polymeric composition of claim 1, wherein the composition further comprises a plasticizer.

20. The biocompatible, polymeric composition of claim 1, further comprising a therapeutic agent.

21. The biocompatible, polymeric composition of claim 20, wherein said therapeutic agent is selected from the group consisting of anti-inflammatory agents, anti-adhesion agents, osteogenesis and calcification promoting agents, antibacterial agents and antibiotics, immunosuppressive agents, immunostimulatory agents, anesthetics, cell/tissue growth promoting factors, anti-scarring agents, anti-neoplastic and anticancer agents.

22. The biocompatible, polymeric composition of claim 20, wherein said therapeutic agent is an antibiotics selected from the group consisting of erythromycin, penicillins, cephalosporins, doxycycline, gentamicin, vancomycin, tobramycin, clindamycin and mitomycin.

23. The biocompatible, polymeric composition of claim 20, wherein said therapeutic agent is a osteogenesis and calcification promoting agent selected from the group consisting of hydroxyapatite and collagen.

24. A biocompatible, polymeric composition, comprising:
   an absorbable polyaxial block copolymer;
   wherein the absorbable polyaxial block copolymer comprises repeat units derived from cyclic monomers selected from the group consisting of para-dioxanone, L-lactide, D-lactide, D,L-lactide, glycolide, caprolactone and trimethylene carbonate;
   wherein the absorbable polyaxial block copolymer further comprises a polyaxial prepolymer;
   a semicrystalline end-graft, and
   a third outer segment.

25. The biocompatible, polymeric composition of claim 24, wherein the third outer segment comprises repeat units derived from trimethylene carbonate.

* * * * *